Figure 1:
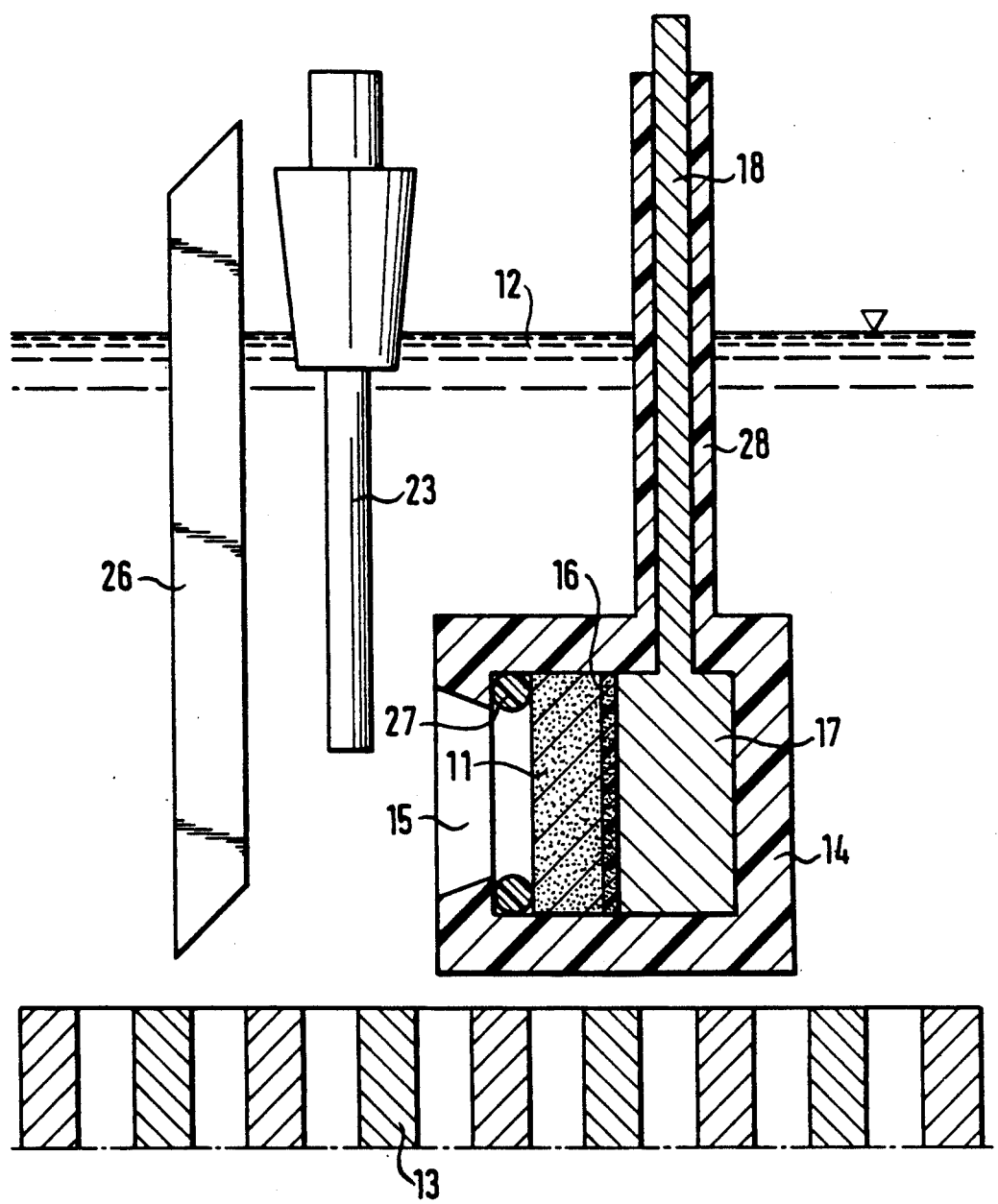

United States Patent [19]

Beck et al.

[11] Patent Number: 4,988,418

[45] Date of Patent: Jan. 29, 1991

[54] METHOD OF ELECTRICALLY MEASURING THE CONCENTRATION OF ACIDS

[75] Inventors: Fritz Beck, Duisburg; Holger Krohn, Mülheim; Rainer Wagner, Dortmund; Eberhard Nann, Soest-Deiringsen, all of Fed. Rep. of Germany

[73] Assignee: Hagen Batterie AG, Soest, Fed. Rep. of Germany

[21] Appl. No.: 323,534

[22] Filed: Mar. 14, 1989

[30] Foreign Application Priority Data

Mar. 18, 1988 [DE] Fed. Rep. of Germany ....... 3809247

[51] Int. Cl.[5] ............................................. G01N 27/26
[52] U.S. Cl. ............................. 204/153.1; 204/153.21; 204/400; 204/402; 204/412; 204/433; 204/434
[58] Field of Search ............... 204/1 T, 1 H, 400, 402, 204/433, 434, 412, 153.1, 153.21

[56] References Cited

U.S. PATENT DOCUMENTS 4,505,784 3/1985 Mund et al. .......................... 204/402
4,566,949 1/1986 Berger .................................. 204/402

FOREIGN PATENT DOCUMENTS 1531761 11/1978 United Kingdom ................ 204/402

OTHER PUBLICATIONS

Beck et al, "Graphite Intercalation Compounds as Positive Electrode in Galvanic Cells", *Electrochem Acta*, (26), 1981, pp. 799–809.

*Primary Examiner*—T. Tung
*Attorney, Agent, or Firm*—Townsend and Townsend

[57] ABSTRACT

In a method for the electrical measurement of the concentration of acids a measurement electrode (11) consisting at least predominantly of crystalline graphite is arranged in an acid (12) having anions which form graphite intercalation compounds with graphite. The measurement electrode (11) is then intercalated by generating in the measurement electrode (11), at a variable positive potential, a current of such a size that the anions of the acids (12) can from graphite intercalation compounds with the graphite. The current is maintained until the intercalation compounds have formed at the surface. The potential at the measurement electrode (11) is then measured and used as a measure for the acid concentration. The measurement electrode (11) is subsequently deintercalated again.

20 Claims, 5 Drawing Sheets

METHOD OF ELECTRICALLY MEASURING THE CONCENTRATION OF ACIDS

The invention relates to a method for the electrical measurement of the concentration of acids wherein the concentration dependent electrochemical potential of a measurement electrode arranged in the acid and cooperating with an inert counter-electrode, which is likewise arranged in the acid, is measured and the concentration is derived therefrom.

The problem of indicating the state of charge of rechargeable batteries, in particular lead accumulators, has hitherto not been even approximately satisfactorily solved. For the lead accumulator the acid density is known to be a clear function of the state of charge. The discontinuous detection of the acid density by means of an areometer (hydrometer) is complicated and awkward. Other methods of continuously measuring the electrolyte concentration have also already been proposed, for example the detection of the extension in length of an ion exchange foil which is immersed in the electrolyte (DE-OS 22 54 207), or the continuous measurement of the relative air humidity above the electrolyte with the aid of the conductivity of a solid electrolyte (Journal of Electrochemical Science, 129, 2409). These known methods for the continuous measurement of the electrolyte concentration are however complicated and expensive. The direct measurement of the electrolytic specific conductivity does not lead to a unique concentration determination since the measurement values at the center of the usable concentration range of the sulphuric acid extend over a broad maximum. In the prior art there is thus a lack of a reliable method which can really be used in every case for indicating the quantity of current or energy which is still present in the battery or in the accumulator. Above all, the known measuring methods are generally not suitable for determining the acid concentration in outwardly closed systems. Problems in measuring the acid concentration however arise when the electrolyte is present as a gel or the acid is bound in a fleece.

The object of the invention is thus to provide a method of the initially named kind with which a continuous, accurate reliable and relatively simple measurement of the concentration of an acid, in particular of sulphuric acid in a lead accumulator, is possible over a broad range of concentrations, with the measurement result being present in the form of an electrical signal. The method should also be suitable for use in outwardly closed systems, in particular lead accumulators having no filling openings or accumulators in which the electrolyte is present as a gel or bound in a fleece.

In order to solve this object the invention provides that the measurement electrode consisting at least predominantly of crystalline graphite is arranged in an acid having anions which form graphite intercalation compounds with graphite; in that the measurement electrode is intercalated by generating a current in the measurement electrode at a variable potential with the current being of such a size, that the anions of the acid can form the graphite intercalation compounds; in that the current is maintained until the graphite intercalation compound has formed at the surface; in that the potential of the measurement electrode which arises at the start of the formation of the graphite intercalation compound is measured and used as a measure for the acid concentration; and in that, before a formation of the graphite intercalation compound arises which goes substantially beyond the surface, a negative potential is applied to the measurement electrode of a size such that the measurement electrode is deintercalated again.

The concept underlying the invention is thus to be seen in the fact that the formation of graphite intercalation compounds is permitted only to the extent that the relatively constant potential which arises with the sudden increase in current at the start of formation of the graphite intercalation compounds is measured at the measurement electrode, and in that immediately after this measurement the graphite intercalation compounds are removed again as rapidly as possible through the application of a negative potential in order to effectively avoid corrosion of the measurement electrode and thus premature destruction of this electrode.

It is already known that graphite can form graphite intercalation compounds. This is a reversible electrochemical process. Furthermore, the pronounced linear concentration dependence of the intercalation potential is known (Electrochim Acta 26, 799 to 809; 1981). With an increase of the acid concentration by 1 mol/l the potential of the electrode consisting of graphite is displaced by approximately 60 mV for sulphuric acid and by approximately 30 mV for hydrofluric acid in the negative direction over the entire concentration range from 0.1 M to 100%.

A stationary electrode consisting of a graphite intercalation compound which is submerged into an acid delivering the anions is however not suitable as a measurement electrode for permanent operation, since a slow self-discharge occurs. As the potential of this electrode also depends on the state of charge, with the potential changing in a reversible range by ca. 500 mV a unique concentration measurement is not possible. When fully discharged the potential would fall into the region of the quinones/hydroquinones (in German Chinons/Hydrochinons). On overcharging the graphite material would be irreversibly destroyed with the formation of graphite oxide.

As a result of the method of the invention a reliable electrical proportional measurement of the acid density is also possible in longer term use, since the measurement electrode is in each case only charged up so far in one period that a measurement of the intercalation potential is possible. After the relevant measurement the measurement electrode is again immediately discharged whereby destruction of the graphite material is effectively avoided and an exact and precise association between the intercalation potential and the concentration is ensured.

It is thus important for the invention that the graphite electrode or probe is always only intercalated at the surface, and that after determination of the intercalation potential it is at once deintercalated again.

Under intercalation one understands the storage of anions in the graphite lattice, for example anodic $HSO_4$ and undissociated H in accordance with the reaction:

$$C_x + HSO_4^- + H_2SO_4 \rightleftharpoons [C_x^+HSO_4^-.2H_2SO_4] + e^-.$$

The potential at which the storage commences is named the intercalation potential; it is relatively strongly dependent on the acid concentration or acid density.

Since the measurement of the rest potential of the graphite intercalation compound (which is in principle possible and particularly simple) is not practical because of the restricted stability of these compounds in diluted acids, use is made of the dynamic pulse method in accordance with the invention in which intercalation and deintercalation are alternatingly carried out at the graphite sensor, i.e. at the graphite measurement electrode. The electrode is in this manner repeatedly returned into the stable non-charged state. The measurement electrode which operates in accordance with the method of the invention has an unusually long life. The method is suitable for the concentration determination of all acids of which the anions are intercalated, for example hydrofluric acid, perchloric acid, sulphuric acid etc. With sulphuric acid a range of use results for concentrations greater than 0.2 M and temperatures up to 65° C.

A first practical embodiment of the method of the invention is characterised in that the measurement electrode is polarised in the anodic direction while measuring the potential with a constant low current density until a section is achieved which is very flat and in particular that the rise in potential within 0.2 sec lies below 5 mV (dU/dt<25 mW/sec) with the potential at which this occurs for the first time being used as a measure for the acid concentration; and in that deintercalation is subsequently effected with a constant low current density in the cathodic direction.

The current is preferably reversed after reaching the section where the potential remains constant. The current density normally amounts to 0.01 to 10 mA . cm$^{-2}$, preferably to 1 to 3 mA . cm$^{-2}$ and in particular to approximately 2 mA . cm$^{-2}$. A current free pause of preferably several minutes, in particular 5 minutes should preferably be proficed after the deintercalation.

The measurement principle described immediately above is termed the galvanostatic measurement principle. A large advantage of this measurement method lies in the fact that just one pulse is sufficient for the determination of the intercalation potential, so that the measurement electrode can remain at the rest potential until the next measurement. The galvanostatic measurement principle is particularly advantageous since it can be carried out in practice in a very simple manner and since it delivers particularly accurate concentration measurement results, and indeed independently of whether the measurement electrode is brought from an acid of lower concentration into an acid of higher concentration or vice versa.

A further practical embodiment which is termed a potentiostatic measurement is characterised in that a base potential on which alternate positive and negative pulses are superimposed is applied to the measurement electrode and the resulting current is measured, with the base potential being increased from a value where, on the occurrence of the positive pulse, no substantial formation of graphite intercalation compounds occur, up to a value where, on occurrence of the positive pulse, an intercalation current flows in jump-like manner; and in that the base potential or the sum of the base potential and the preferably constant positive pulse is used as a measure for the concentration. As soon as the base potential has reached the value at which a clear intercalation current flows at the end of the positive pulse the intercalation potential has been achieved and can be evaluated to determine the acid concentration.

Figure 5:
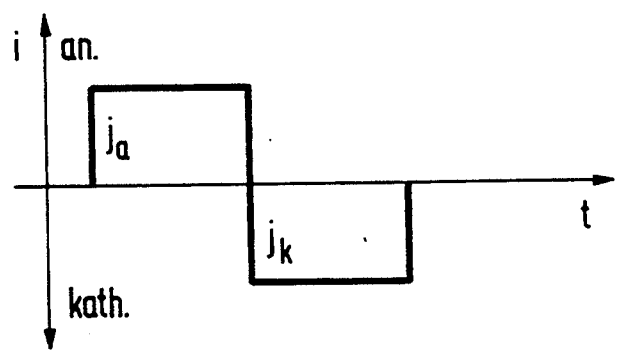

In order to determine the association between the intercalation potential and the concentration, calibration curves can be prepared for each available measurement electrode and the associated acid, for example calibration curves such as are known from FIG. 5 on page 803 of Electrochim. Acta 26, 1981.

The measurement electrode advantageously consists of Acheson-graphite, resin-bound natural graphite, natural graphite, pyrolytic graphite (HOPG) or a composite material comprising a plastic binder and natural graphite flakes, in particular 80% natural graphite flakes and 20% polypropylene.

By way of example a mixture of a plastic binder and natural graphite flakes can be extruded and then pressed in a hot press at elevated temperature, in particular 190° C. into a non-porous plate.

Alternatively the measurement electrode can comprise synthetic metals such as poly-p-phenylene, polypthiophene or other conducting polymers. The measurement electrode is usefully used to measure the state of charge of an accumulator, in particular a lead accumulator filled with sulphuric acid as electrolyte. In this case the measurement electrode can additionally be used as an acid level measuring device in that the measurement electrode is arranged above the plates of the accumulator and simultaneously serves as an acid level measuring device.

The invention is used with particular advantage in a method in which the electrodes are arranged in a fixed electrolyte, for example an electrolyte in the form of a gel or fixed in a fleece, and can be used at acid concentrations which are the same as or larger than 0.2 mol/l, with an acid concentration of 0.5 to 1 mol/l preferably being present in the measurement electrode during the measurement.

A preferred embodiment of a measurement electrode for the method of the invention is characterised in that a plate having a crystalline graphite is sealingly arranged at an opening of a housing of acid resistant plastic and is electrically conductively connected via a blocking plate of carbon filled plastic with an outward leading copper conductor.

A preferred apparatus for carrying out the method of the invention is characterised in that a potentiostat or galvanostat connected to the measurement electrode is controlled via a digital/analog converter from a computer; and in that, with the galvanostatic method, either the potentials of the measurement electrode and optionally a reference electrode, or, with a potentiostatic method, the current through the measurement electrodes are applied via an analog/digital converter to the computer at the output of which a charge state indication is provided.

Figure 2:
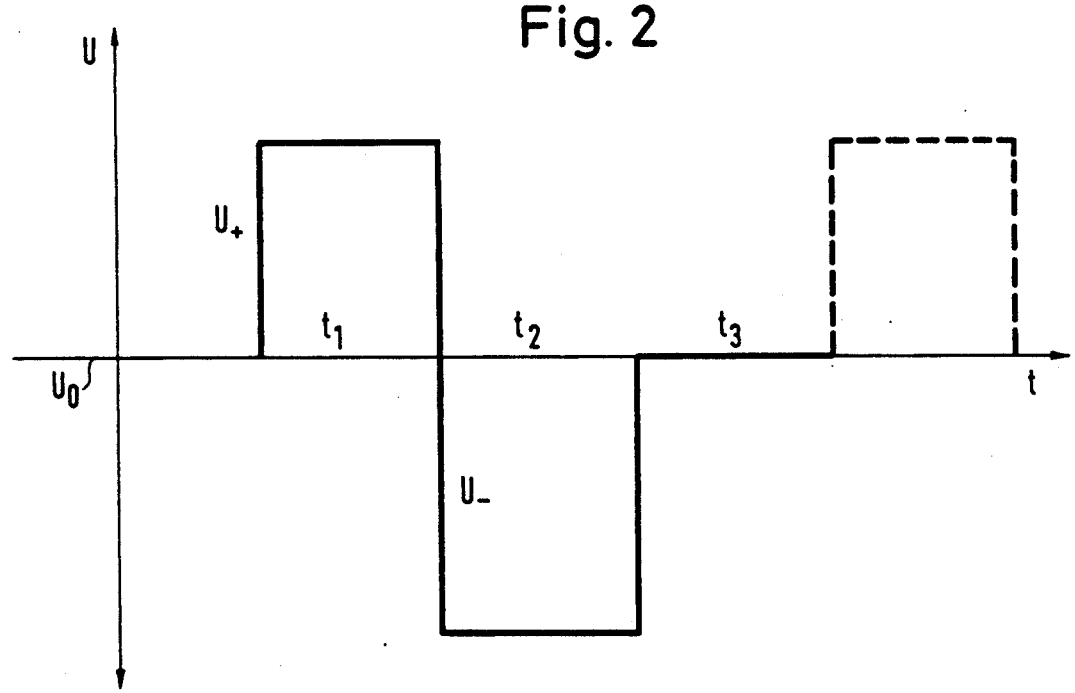
Figure 3:
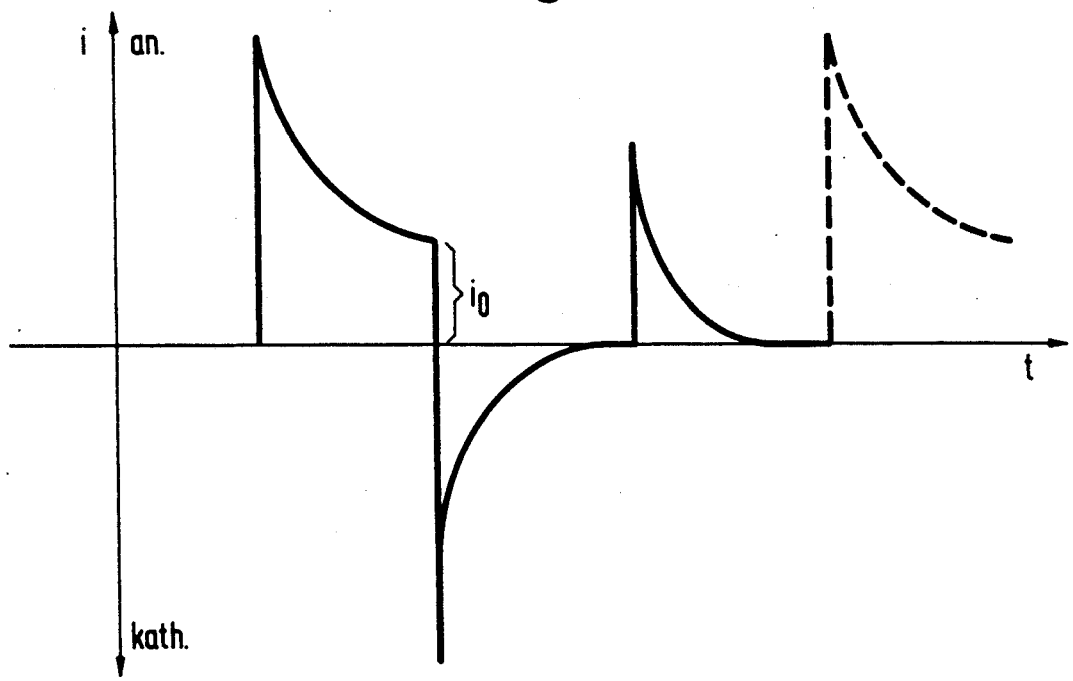
Figure 4:
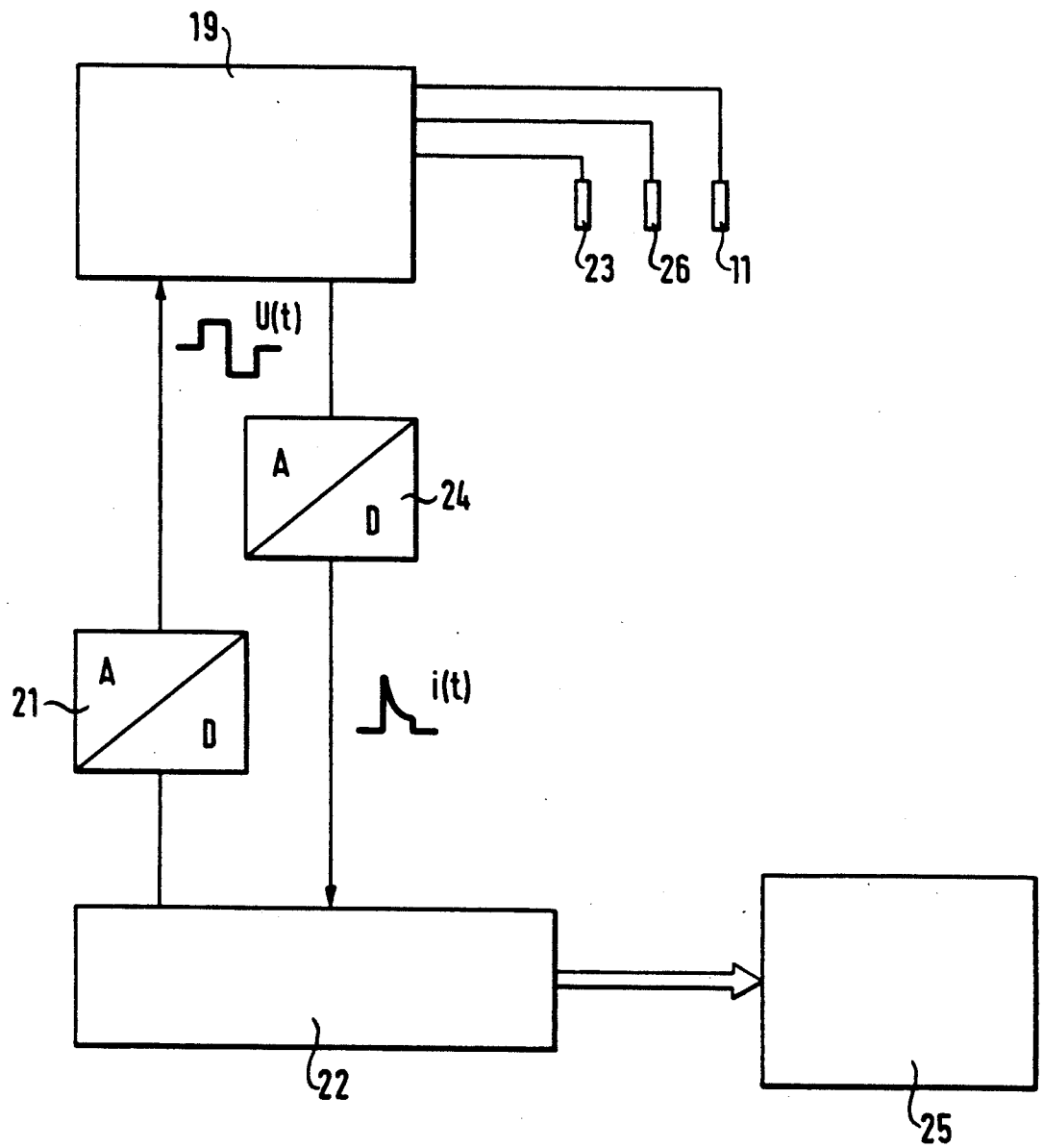
Figure 6:
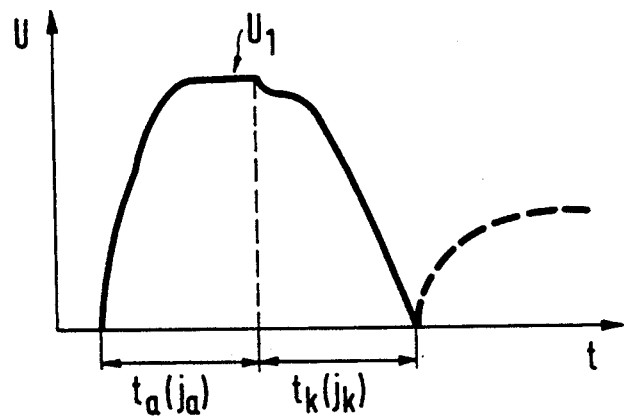
Figure 7:
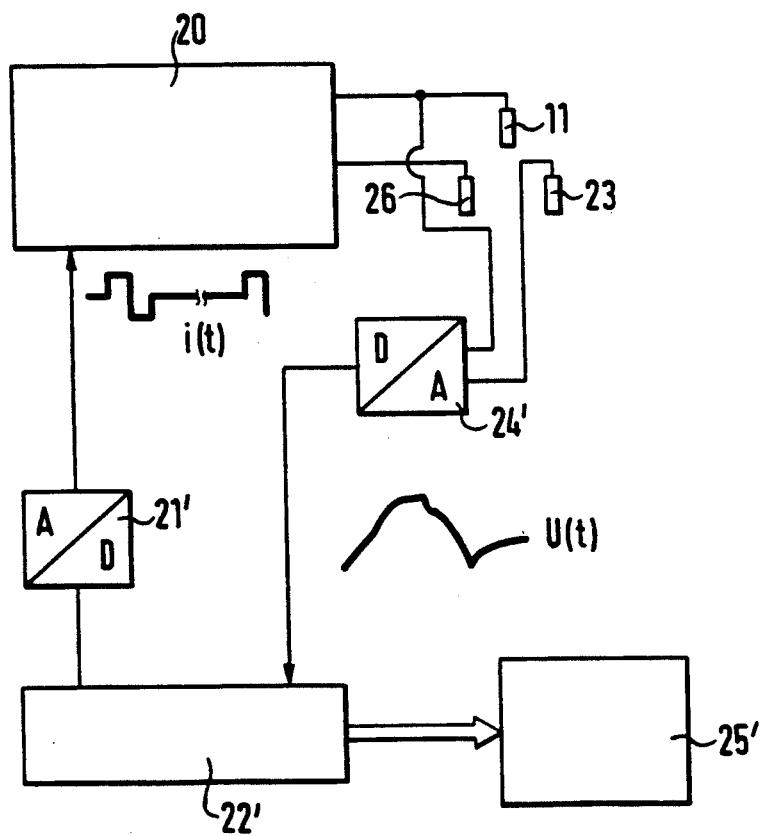
Figure 9:
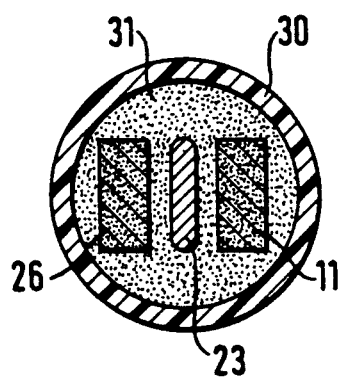
Figure 8:
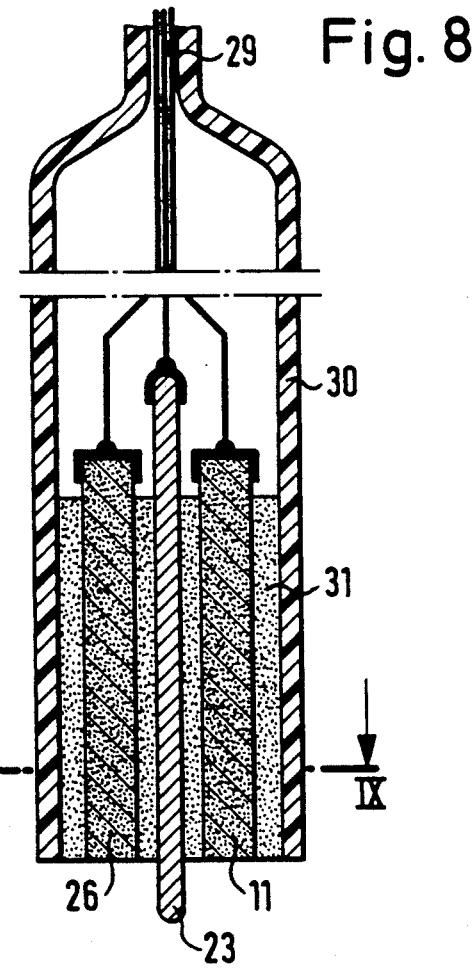
Figure 10:
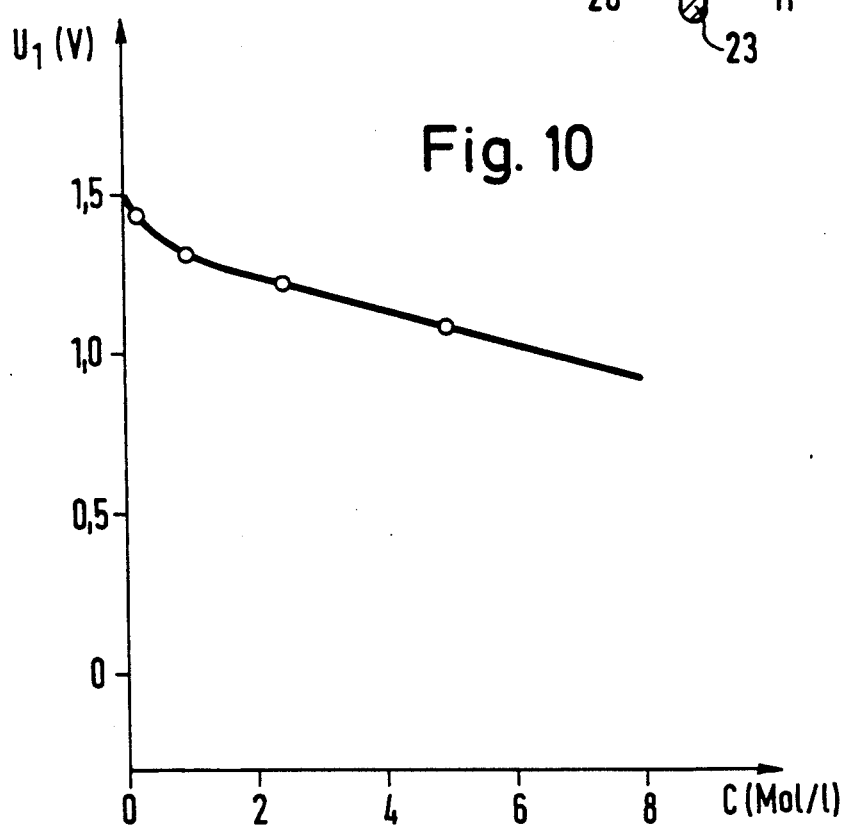

The invention will now be described in detail in the following with reference to examples and to the drawing in which are shown:

FIG. 1 a schematic illustration of a section of a lead accumulator filled with dilute sulphuric acid and having three electrodes which are necessary for carrying out the method of the invention, FIG. 2 a potential/time diagram for the potentiostatic embodiment of the method of the invention, FIG. 3 the current/time diagram belonging to FIG. 2, FIG. 4 a block diagram of an apparatus for carrying out the potentiostatic measurement method of the invention, FIG. 5 a current/time diagram of the galvanostatic embodiment of the measurement method of the invention, FIG. 6 the potential/time diagram which belongs to FIG. 5, FIG. 7 a block circuit diagram of an apparatus for carrying out the galvanostatic measurement method of the invention, FIG. 8 a vertical central longitudinal section of a further embodiment of a measurement electrode for carrying out the measurement method of the invention, FIG. 9 a section on the line XI—IX in FIG. 8 and FIG. 10 a calibration diagram of a graphite measurement electrode cooperating with sulphuric acid in accordance with the present invention, with the sulphuric acid concentration in mol/l being recorded on the abscissa and the potential of the graphite measurement electrode relative to the $Hg/Hg_2SO_4/1$ M $H_2SO_4$ reference electrode being recorded in V on the ordinate.

As seen in FIG. 1 a measurement electrode 11 consisting of crystalline graphite, a counter-electrode 26 consisting for example of crystalline graphite or lead and likewise inert relative to the electrodes and the applied potentials and a reference electrode 23 consisting for example of $Hg/Hg_2SO_4$ are arranged in a non-illustrated housing of a lead accumulator filled with sulphuric acid 12 above the plate set 13. The plate set 13 consists of negative and positive plates and also separators. These electrodes are supplied with voltage and current by a potentiostat 19 in a manner which will be described later with reference to FIG. 4. A defined potential as will be explained further below with reference to FIG. 2 is applied by the potentiostat 19 between the reference electrode 23 and the measurement electrode 11 while the measurement takes place with reference to the current diagram explained in FIG. 3 between the measurement electrode 11 and the counter-electrode 26.

The plate-like graphite measurement electrode 11 is arranged behind the lateral opening 15 of a housing 14 of an acid resistant plastic and is sealed relative to the interior of the housing 14 by a 0-ring 27 provided between the edge of the opening 15 and the measurement electrode. The front side of the plate-like measurement electrode 11 is thus exposed to the sulphuric acid 12. At the rear side of the plate-like measurement electrode 11 there is a blocking plate 16, for example of a soot-filled plastic which stands in electrically conducting connection with both the measurement electrode 11 and also a copper block 17 arranged at the rear side. The copper block 17 and the blocking plate 16 are likewise closely surrounded by the plastic housing 14. A possible diffusion of intercalation anions through the measurement electrode 11 through to the copper contact is completely prevented by an intermediate soot-filled polycarbonate foil. The blocking plate 16 can also consist of a thin gold or platinum foil or a coating of hard substances such as silicon nitride or titanium carbide.

The plastic housing is held by a tube 28 of acid resistant plastic which projects upwardly out of the sulphuric acid 12 with a copper conductor 18 which is in electrically conducting connection with the copper block 17 being located in the interior of the tube 28 and being connected to the potentiostat 19 of FIG. 4.

In accordance with the invention a non-illustrated thermal sensor can be integrated on or in the housing 14 in the region of the measurement electrode 11 in order to be able to effect the temperature corrections that are required.

The electrode 23 is a $Hg/Hg_2SO_4/1$ M $H_2SO_4$ reference electrode (M signifies Mol/l) while the counter-eletrode 26 takes the form of a strip of sheet lead.

In accordance with FIG. 4 the electrodes 11, 23, 26 are supplied by the potentiostat 19 with suitable potentials and currents in the manner which will be described in detail in the following. The potentiostat is controlled via a digital/analog converter 21 from a computer 22 (FIG. 4). The currents which flow between the electrodes are determined by the potentiostat 19 and passed via an analog/digital converter 24 to the computer 22. The output signal of the computer 22 is delivered to a charge state indicator 25 which indicates the state of charge in a suitable manner, for example on the scale of a measurement instrument.

The computer controlled potentiostat 19 applies a voltage such as is schematically illustrated in FIG. 2 to the measurement electrode 11. Constant voltage pulses $U_+$ and $U_-$ are superimposed in the manner which can be seen from FIG. 2 on a base potential $U_0$. The positive voltage pulse $U_+$ has an amplitude of 20 to 100 mV relative to the base potential $U_0$. The voltage pulse must be so constructed that the flank of the current-voltage curve is somewhat cut.

The potentiostat 19 also measures the current i which is flowing through the measurement electrode 11 and which is reproduced in the correct time association in the diagram of FIG. 3.

One can see that after the start of the positive voltage pulse $U_+$ the current rises abruptly. The potential $U_0$ is thereby so restricted that on the appearance of a voltage pulse $U_+$ which is to be added thereto a relatively small current only flows over a very short period, i.e. one moves only very little into the intercalation range. The control of the potential $U_0$ which is effected by the potentiostat is thus so selected that one always remains in the first rising region of the current density - potential curve. In detail the measurement process takes place in the following way:

Starting from a first value $U_0$ the potential is increased in accordance with FIG. 2 by $U_+$. If the current lies below a predetermined threshold value at the end of the $U_+$ pulse the $U_0$ is increased by a predetermined amount $\Delta U$ and the measurement cycle is repeated. The increase of $U_0$ by small amounts is increased until the current at the end of the pulse $U_+$ has reached or exceeded a predetermined threshold value $i_0$. The size of $i_0$ is to be selected such that the current at the end of the $U_+$ pulse already contains a notable component of the intercalation current. The relatively high current which is present at the start of the $U_+$ pulse drops away rapidly in accordance with FIG. 3 since it contains the unavoidable charging of the electrochemical double layer; the current however also contains an intercalation of the anions which drops away rapidly due to concentration polarisation.

In this connection it should be pointed out that the double layer capacity of a graphite measurement electrode of the invention is higher by the factor of 1000 than with customary electrodes. The pulse time $t_1$ is so selected that at the end of this period there is only a pure intercalation current $i_0$ which is flowing, i.e. at this time point the double layer capacitor is practically charged up. $i_0$ is used by the computer 22 (FIG. 4) as a regulating parameter.

If the predetermined intercalation current $i_0$ is achieved after the time $t_1$ then, in accordance with FIG. 2, the negative voltage pulse $U_-$ is applied, the absolute value of which clearly exceeds the voltage pulse $U_+$. The measurement electrode 11 is in this way immediately discharged again. The current i drops off within a second time period $t_2$ practically to zero. As soon as the value 0 is achieved the negative voltage pulse $U_-$ in accordance with FIG. 2 which is also correspondingly timewise restricted is also terminated. The measuring electrode 11 is again in the initial state at the base potential $U_0$.

The measurement electrode 11 now remains for a period $t_3$ at the base potential $U_0$. At the expiry of this rest period a new pulse cycle is started. When using sulphuric acid it is expedient to keep the voltage and time parameters within the following ranges:

$U_+$: 20 to 100 mV
$U_-$: 150 to 500 mV
$t_1$: 0.2 to 2 sec
$t_2$: 1 to 5 sec
$t_3$: 2 sec.

$i_0$ is restricted to a few mA. cm$^{-2}$. The parameter $U_0$ which is uniquely dependent on the concentration is detected from a technical measuring viewpoint by the computer 22 (FIG. 4). $U_0$ can be used for the measurement since the parameter $U_0 + U_+$ which represents the intercalation potential has a fixed relationship to $U_0$ since $U_+$ is a constant value.

The computer 22 of FIG. 4 selects the base potential $U_0$ automatically so that $i_0$ is not exceeded as a control parameter.

The computer displays the state of charge or the acid concentration on the charge state indicator 25 in dependence on the determined intercalation potential.

If one submerges the measurement electrode 11 in an electrolyte of unknown sulphuric acid concentration then the control system requires ca. 10 pulse sequences until the intercalation threshold has been reached. $U_0$ is gradually increased stepwise with $U_+$ remaining constant by amounts $\Delta U$ (which can expediently adopt values between 0 and 10 mV) until the new equalisation is realised (desired value of $i_0$ is 0.8 mA/cm$^2$) with gradually changing concentrations very many fewer pulses are required to reach the regulation point.

A galvanostatic measuring principle which is an alternative to the potentiostatic measurement method will now be described in the following with reference to FIGS. 5 to 7. A computer 22' controls via a digital-/analog converter 21', a galvanostat 20 which energises the measurement electrode 11 with a pulse current in accordance with FIG. 5. The rectangular pulse current consists of positive half waves $j_a$ and negative half waves $j_k$. A constant low current density of 0.01 to 10 mA . cm$^{-2}$ is maintained during both half waves. During the positive half wave the measurement electrode 11 is polarised in the anodic direction. During this the potential U increases with a time $t_a$ up to the intercalation potential $U_1$; the potential of the measurement electrode 11 hereby changes through a potential range of the order of magnitude of approximately 1 V, with the charging of the electrochemical double layer, the change of charge of the quinone surface groups and the formation of higher intercalation stages at the graphite surface taking place in complicated manner. Finally, however, a section of almost constant potential $U_1$ is reached. If one then reverses the current a short time after reaching the intercalation potential $U_1$ (negative half wave $j_k$) then the measurement electrode 11 is discharged again for which purpose a time $t_k$ is necessary.

The precise determination of the intercalation potential $U_1$ takes place in such a way that in the part of the potential curve of FIG. 6 which flattens off, the potential rise is measured at intervals of for example 0.2 sec. If this potential rise falls for the first time below 5 mV (i.e. $dU/dt < 25$ mV . sec$^{-1}$) then this value is retained as the end value $U_1$. In an advantageous variant $U_1$ is the average value of the two last end values below 5 mV per 0.2 sec.

In a third variant the poles are first reversed when the potential rise falls for a third time in sequence below 5 mV in 0.2 sec and the average value from the last two or from the last three measurements is found. The current is reversed on reaching the so defined $U_1$ value.

The current program of FIG. 5 is preset by the computer 22' illustrated in FIG. 7. The electrodes 11, 23, 26 are connected via an analog/digital converter 24' to the computer 22' which analyses the potential/time curve in the above sense. The $U_1$ value is finally indicated by the computer in the charge state indicator 25' as a measure for the acid concentration.

A substantial advantage of the galvanostatic measurement method lies in the fact that only a pair of positive and negative current pulses is sufficient to detect the intercalation potential $U_1$, so that the measurement electrode 11 can remain at a rest potential until the next measurement.

Typical values for the pulse program delivered by the computer 22' in accordance with FIG. 7 and shown in FIG. 5 are:

$i_a = i_k = 1$ mA (surface A of the measurement electrode 11 of the order of 0.5 cm$^2$)

$t_a = t_k = 1$–10 sec $t_0 = 5$ min.

A measurement electrode 11 which can be better used in practice than the measurement electrode of FIG. 1 and which can be made substantially smaller is shown in FIGS. 8 and 9.

The measurement electrode 11 and the counter-electrode 26 and also between them the reference electrode 23 are cast insulated from one another in epoxy resin 31 in a housing 30 of polypropylene. The feedlines 29 to the electrodes 11, 23, 26 enter into the housing at the top and the housing is open at the bottom. The electrodes 11, 26 have the same relatively large rectangular cross-section whereas the reference electrode 23 arranged between them has a substantially smaller elongate cross-section. It is arranged parallel to the electrodes 11, 12 which are in turn parallel to each other.

Whereas the measurement electrode 11 and the counter-electrode 26 consist of natural graphite composite material with for example 80% natural graphite flakes and 20% polypropylene, the reference electrode 23 is manufactured from cadmium. The latter electrode 23 projects downwardly in the manner shown in FIG. 8 somewhat beyond the electrodes 11, 26 which are cut-off perpendicular to the axis of the housing 30.

The fact that the two electrodes 11, 26 are cut-off at the lower end of the housing perpendicular to their axes means that optimum conditions are present for the intercalation. The upper ends of the three electrodes 11, 23, 26 are copper plated and provided with a soldered wire contact. A diffusion barrier in the form of a soot-filled plastic foil can optionally be provided here as in the embodiment of FIG. 1.

The reference electrode 23 can also be a Hg/Hg$_2$SO$_4$ electrode of the second kind.

The electrodes 11, 23, 26 preferably consist of the above described materials even with a different realisation than in FIGS. 8 and 9.

In the following the electrode material which is preferably used will be once again summarised.

The measurement electrode 11 consists wholly or partially of a graphite material. It can be formed from a synthetic material such as poly-p-phenylene or polythiophene.

The counter-electrode 26 consists of a conductive material which is inert against acids such as for example materials of the measurement electrode, furthermore of lead, gold, platinum, platinised tantalum, hard metals such as silicon nitride or titanium carbide. It can also be advantageously formed from soot-filled plastics.

The reference electrode 23 must be compatible with the acid solutions and maintain a constant reference potential. In the following a few systems will be named by way of example:
(a) acid mercury/mercury-I-sulfate electrodes;
(b) cadmium electrodes;
(c) graphite electrodes with a high surface concentration of quinone surface groups. They are formed by a 1 to 24 hour a.c. polarisation (50 Hz) of a graphite electrode at a current density of 10 mA/cm$^2$ in 1 M H$_2$SO$_4$ and represent a particularly priceworthy variant of a reference electrode.

FIG. 10 shows a typical dependence of the intercalation potential of a graphite measurement electrode 11 in dependence on the sulphuric acid concentration in Mol/l.

The intercalation potential U$_1$ was determined in accordance with the galvanostatic measuring process described with reference to FIGS. 5 to 7.

All the following examples can be given of acids, the concentration of which can be technically determined in a wide range, with these acids having anions which can be intercalated. These examples include:

| | |
|---|---|
| sulphuric acid | H$_2$SO$_4$ |
| perchloric acid | HClO$_4$ |
| hydrofluoric acid | H$_2$F$_2$ |
| tetrafluoroboric acid | HBF$_4$ |
| trifluoroacetic acid | CF$_3$COOH |
| methane sulphonic acid | CH$_3$SO$_3$H and |
| hexafluorophosphoric acid | HPF$_6$. |

The measurement electrode of the invention operates reliably in the temperature range between 0 and 50° C. At temperatures below 0°, the adjustment time can become slower. At temperatures above 50° C. the indication ca eventually become inaccurate since the current voltage curve no longer rises so steeply and since the self-discharge becomes large.

The invention will now be described in the following with reference to two examples:

EXAMPLE 1

An arrangement in accordance with FIG. 1 with a measurement electrode 11 in the form of a round plate of a composite material consisting of 20% by weight of polypropylene and 80% by weight of natural graphite flakes had a diameter of 10 mm and a thickness of 3 mm. It was used to measure the sulphuric acid concentration in the range from 0.2 Mol/l to 5 Mol/l. Prior to use the measurement electrode 11 was roughened slightly on the side facing the sulphuric acid 12 (FIG. 1) with emery and was subjected, in position in the holder of FIG. 1, for forming purposes to a galvanostatic a.c. polarisation for a period of 10 hours at a constant current density of ±1 mA . cm$^{-2}$ and a frequency of 0.5 Hz in 7 M H$_2$SO$_4$.

The charge and discharge cycles of a technical lead battery was subsequently simulated with the aid of a laboratory robot. The latter immersed the probe into respective glass beakers with 1 l of H$_2$SO$_4$ of the concentration 5 Mol/l, 2.5 Mol/l, 1 Mol/l, 0.5 Mol/l and 0.2 Mol/l.

The galvanostatic measurement process explained with reference to FIGS. 5 to 7 was used with the following values:

$$i_a = 2 \text{ m A/cm}^2$$

$$i_k = 2 \text{ m A/cm}^2$$

$$t_a = 1\text{-}10 \text{ sec}$$

The U$_0'$ values were printed out in the space of 5 minutes, i.e. 12 times per immersion. In the exchange periods the measurement electrode was separated automatically from the galvanostat 20 in order to avoid overloading the measurement electrode 11.

The U$_0'$ print-outs after 1000 hours corresponding to 100 simulated charge and discharge circles were evaluated. From this the following picture arose, with the molar concentration of the sulphuric acid being given in the first column and the U$_0$ values given in the second column:

| c (Mol/l) | U$_1$ (V) |
|---|---|
| 5.0 | 1.067 |
| 2.5 | 1.209 |
| 1.0 | 1.303 |
| 0.5 | 1.371 |
| 0.2 | 1.437 |

The Hg/Hg$_2$SO$_4$/1 M H$_2$SO$_4$ electrode was used as the reference electrode 23.

EXAMPLE 2

In a production plant for aqueous hydrofluoric acid with a concentration of 60% by weight the acid concentration was kept constant by the metered supply of HF gas or H$_2$0. To control the metering devices a measurement electrode in accordance with the invention was submersed into the product. The manner of operation of the measurement electrode 11 took place in accordance with the potentiostatic principle and the measurement value, which was shown in the form of a voltage U$_0$ which is proportional to the acid concentration, reproduced the concentration of the hydrofluoric acid precisely over a long time.

We claim:

1. Method of electrically measuring a concentration of an acid wherein a concentration dependent electrochemical potential of a measurement electrode arranged in the acid and cooperating with an inert counterelectrode, which is likewise arranged in the acid, is measured relative to a suitable reference electrode and the concentration is derived therefrom, characterised in that a measurement electrode (11) comprising crystalline graphite is arranged in an acid (12) with intercalatable anions; in that the measurement electrode is intercalated; in that an anodic current of a suitable size is directed through the measurement electrode; in that the current is maintained until a graphite intercalation compound has formed at the surface of the measurement electrode; in that the potential of the measurement electrode which arises at the start of the formation of the graphite intercalation compound is measured and used as a measure for the acid concentration; and in that, before the formation of the graphite intercalation compound arises which goes substantially beyond the surface, the current is reversed or a negative potential is applied to the measurement electrode of a size such that the measurement electrode is deintercalated again.

2. Method in accordance with claim 1, characterized in that the measurement electrode (11) is polarized in the anodic direction while measuring the potential with a constant low current density until a rise in potential within 0.2 sec lies below 5 mV, the potential at which this occurs for a first time being an intercalation used as the measure for the acid concentration; and that deintercalation is subsequently effected with a constant low current density in a cathodic direction.

3. Method in accordance with claim 2, characterized in that the current is reversed after the intercalation potential remains constant.

4. Method in accordance with claim 2, characterized in that the current density amounts to 1 to 3 mA . cm$^{-2}$.

5. Method in accordance with claim 2, characterized in that a current-free pause of 5 minutes is provided after the deintercalation.

6. Method in accordance with claim 1, characterized in that a base potential on which alternate positive and negative pulses are superimposed is applied to the measurement electrode (11) and the resulting current is measured, with the base potential being increased from a value where, on the occurrence of the positive pulse, no substantial formation of the graphite intercalation compound occurs, up to a value where, no occurrence of the positive pulse, an intercalation current flows in a jump manner; in that the base potential or the sum of the base potential and the constant positive pulse is used as a measure for the concentration; and in that a negative potential of a size such that the measurement electrode is deintercalated is applied.

7. Method in accordance with claim 6, characterized in that the positive pulse have an amplitude of 30 to 70 mV.

8. Method in accordance with claim 6, characterized in that the negative pulses have an amplitude of 150 to 250 mV.

9. Method in accordance with claim 6, characterized in that the positive pulses have a time length such that the intercalation current at the end of the pulse amounts to 0.1 to 10 mA . cm$^{-2}$.

10. Method in accordance with claim 9, characterized in that the positive pulses have a time length of 0.3 to 1.3 sec.

11. Method in accordance with claim 9, characterized in that the negative pulses have a time length of 1 to 2 sec.

12. Method in accordance with claim 6, characterized in that the measurement electrode (11) is kept at the base potential for a specific time between each negative pulse and the subsequent positive pulse.

13. Method in accordance with claim 12, characterized in that the time is approximately 3 sec.

14. Method in accordance with claim 1, characterized in that the measurement electrode (11) consists of Acheson-graphite, resin-bound natural graphite, natural graphite, pyrolytic graphite or a composite material comprising a plastic binder anD natural graphite flakes.

15. Method in accordance with claim 14, characterized in that the measuring electrode is made by extruding a mixture of plastic binder and natural graphite flakes and then pressing in a hot press in a temperature of 190° C. into a non-porous plate.

16. Method in accordance with claim 1, characterized in that the measurement electrode comprises synthetic metals selected from the group consisting of poly-p-phenylene, polypthiophene and other conducting polymers.

17. Method in accordance with claim 1, characterized in that the measurement electrode (11) is used to measure the state of charge of an accumulator.

18. Method in accordance with claim 17, characterized in that the accumulator is filled with a liquid electrolyte, and the measurement electrode (11) is arranged above plates of the accumulator and simultaneously serves as an acid measuring device.

19. Method in accordance with claim 17, characterized in that the measurement and counter electrodes are arranged in a fixed electrolyte in the form of a gel or an electrolyte fixed in a fleece.

20. Method in accordance with claim 1, characterized in that it is used at acid concentrations of 0.5 to 1 mol/l.

* * * * *